United States Patent [19]

Barak

[11] Patent Number: 4,930,674
[45] Date of Patent: Jun. 5, 1990

[54] SURGICAL STAPLER

[75] Inventor: Jacob H. Barak, Oranit, Israel

[73] Assignee: Abiomed, Inc., Danvers, Mass.

[21] Appl. No.: 315,286

[22] Filed: Feb. 24, 1989

[51] Int. Cl.$^5$ .............................................. A61B 17/00
[52] U.S. Cl. ...................................... 227/179; 227/180; 227/19
[58] Field of Search ..................... 128/334 R, 334 C; 227/19, DIG. 1, 175, 179, 180; 606/149

[56] References Cited

U.S. PATENT DOCUMENTS

| | | | |
|---|---|---|---|
| 2,453,056 | 11/1948 | Zack | 128/334 C |
| 2,940,451 | 6/1960 | Vogelfanger | 227/19 |
| 2,965,900 | 12/1960 | Inokouchi | 227/19 |
| 3,144,654 | 8/1964 | Mallina et al. | 227/19 |
| 3,552,626 | 1/1971 | Astafiev | 227/19 |
| 3,774,615 | 11/1973 | Lim et al. | 128/334 C |
| 4,397,311 | 8/1983 | Kanshin et al. | 128/305 |
| 4,466,436 | 8/1984 | Lee | 227/19 |
| 4,523,592 | 6/1985 | Daniel | 128/334 C |
| 4,708,141 | 11/1987 | Inoue et al. | 128/334 R |

FOREIGN PATENT DOCUMENTS 0725661 4/1980 U.S.S.R. ............ 128/334 R

OTHER PUBLICATIONS

A Stapling Instrument for End-to-end Inverting Anastomoses in the Gastrointestinal Tract, Mark M. Ravitch, M.D., Felicien M. Steichen, M.D.
A Review of Vascular Anastomosis with Mechanical Aids and Nonsuture Techniques, Sun Lee, M.D., Louis Wong, M.D., Marshall J. Orloff, M.D. & Alan M. Nahum, M.D.
A New Type of Vessel-Suturing Apparatus, Kiyoshi Inokuchi, M.D.
A Comparison of the Flow of Iodine 125 through Three Different Intestional Anastomoses: Standard, Gambee, and Stapler, Clifford R. Wheeless, Jr., M.D.
Construction of Internal Arteriovenous Fistuals for Hemdoialysis Using Inokuchi's Vascular Stapler, Naokata Oka et al.
Stapling Techniques in Operations for Malignant Disease of the Female Genital Tract, Clifford R. Wheeless, Jr.
Techniques of Staple Suturing in the Gastrointestinal Tract, Mark M. Ravitch, M.D., Felicien M. Steichen, M.D.

Primary Examiner—Randall L. Green
Assistant Examiner—Gary Jackson
Attorney, Agent, or Firm—Lahive & Cockfield

[57] ABSTRACT

A stapler for the anastomosis of blood vessels includes a vessel gripping structure, and an outwardly directed anvil head structure, and a stapler head structure adjustably positioned opposite each other. A first vessel is everted to form a cuff over one head structure, and the cuff is inserted into the end of, or into a fenestration of, a second vessel. The stapler is then activated to staple the two vessels. In a tong-like embodiment with a pair of linear anvils, a pair of sutures at openings between ends of ranks of staples completes the anastomosis. In a cylindrical embodiment with an enlarged head portion, a circular staple cartridge within the head forms a complete closure ring. In both cases the staples do not communicate with the vessel interior. Methods of end-to-end and end-to-side anastomosis are described. In one stapler instrument the vessel gripping structure is a pair of tongs with opposed outwardly-directed anvils on its jaws. The tongs, stapler arms, staple cartridges and staple drivers may be assembled together during surgery allowing greater access to the blood vessel and ease of manipulation. The construction is adapted to suture different tubular tissue structures.

21 Claims, 11 Drawing Sheets

SURGICAL STAPLER

BACKGROUND

The present invention relates to surgical staplers. A number of such instruments and the basic principals of their design were developed after World War II at the Institute for Experimental Surgical Apparatus and Instruments in Moscow. Subsequently, a good number of particular stapler instruments and surgical techniques for their use in joining particular tissues or performing particular operations have been developed in this country and elsewhere.

Among the commercially developed instruments and accessories now available are such items as pre-loaded staple cartridges in various lengths containing one or two linear rows of staples; disposable and pre-loaded linear staple guns; special cylindrical staplers which are inserted along the interior of the lower intestine for placing a ring of staples for end-to-end anastomosis; and Inokuchi's vascular stapler, which uses pairs of fitted half-bushings and a special staple driver to perform anastomosis of blood vessels.

While stapling has been demonstrated in many surgical contexts to provide better perfusion and enhanced healing of tissue with fewer complications, as compared to conventional manual suturing, there remain a number of particular surgical procedures for which no suitable stapling instrument or technique exists.

Among such procedures are those involving anastomosis bypass and repair of medium to large arteries and veins. Presently, substantially all anastomoses on vessels are done manually. The procedure is time-consuming and requires dexterity and specialized skills; often cross-clamping or bypass are required to carry out the anastomosis. Development of an effective stapler and procedures for its use on medium to large blood vessels may significantly speed up these procedures and reduce morbidity. If such a stapler and procedures for its use can be modified to also work on smaller vessels, further efficiencies of practice may be expected.

SUMMARY OF THE INVENTION

Accordingly, il is an object o( the invention to provide an improved surgical stapler and procedures for autosuturing arteries and veins.

This is achieved in a surgical procedure wherein a first structure both grips a blood vessel and provides a form over which the end of the vessel is everted to form a cuff. Tissue to be joined is placed over the cuff, and a second structure is opposed to the first structure to secure the cuff and tissue therebetween. One of the two structures includes an anvil or base plate, and the other includes a staple cartridge which is actuated to drive staples through the cuff and tissue against the anvil, forming an autosuture connection of the two layers. Sutures may be used in some embodiments to close the gap between ranks of staples around the vessel perimeter.

In one embodiment of the stapler instrument, the first structure includes opposed, outwardly facing anvils. These are defined by a pair of tongs, having generally flat, spatula-shaped jaws with an external gripping surface adjacent an anvil surface on each jaw. The jaws are dimensioned so that a vessel may be gripped between the jaws and everted into a snuggly-fitted cuff over the gripping and anvil surfaces. A pair of arms are removably mounted about the tongs, and hold a linear staple cartridge above each anvil oriented across the axis of the blood vessel. A staple drive member drives the staples from each cartridge. In a preferred embodiment, the jaws accommodate an aorta having a diameter of 18–26 millimeters. A mechanism adjusts the spacing of the arm and anvil to accommodate different thicknesses of vessel tissue without trauma. The tongs, the arms and the staple driving mechanism are each separable from the others to allow clearance for manipulation of a blood vessel during surgery.

In another aspect, the first structure over which the vessel is everted includes a tubular cylinder having an enlarged head or flange at one end. The vessel is placed through a central passage within the cylinder, and the vessel end is everted over the enlarged head and drawn in over the back surface of the head with a purse string about the cylinder. The tip of the first structure is then inserted in the end of, or into a lateral incision of a second vessel such that the tissue of the second vessel overlies the everted tissue over the back surface. A base collar is then positioned opposite the back surface of the head, and a circular ring of staples is driven through the two vessels between the base collar and the head, which contain an appropriately-shaped anvil plate and staple cartridge. A circular knife is then advanced within the base collar to trim the vessels beyond the suture line, and the stapler structure is removed, leaving the first vessel fully sutured by a circular rank of staples to the second vessel.

DETAILED DESCRIPTION

Figure 1:
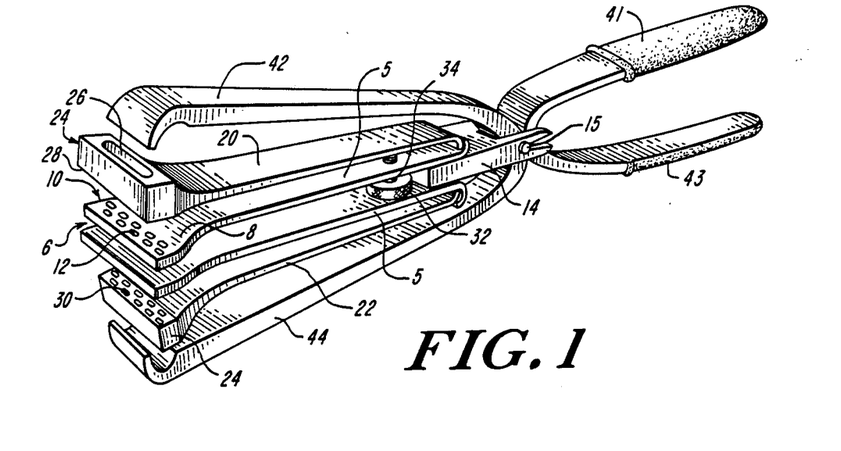
FIG. 1 is a perspective view of one embodiment of the invention.

FIG. 1 illustrates a prototype embodiment of a vascular stapler according to the present invention, to which reference will be made below for the purpose of describing surgical procedures, as well as illustrating certain novel features appearing in the various contemplated embodiments of the invention.

The stapler 1 includes a central pair of tongs 5 each finger of which has a jaw at its gripping end 6 with a broad outwardly directed face 8 including an anvil structure 10 formed thereon. The anvil structure 10 includes curved recesses 12 for bending closed each staple of one or more lines of staples. The tongs 5 have a mounting structure 14 at their handle end, opposite the jaws.

Placed about tongs 5 are a pair of preferably separable stapler arms 20, 22, each of which has a magazine 24 defining a receptacle 26 for holding a surgical staple cartridge in alignment opposite one of the anvils 10. Each magazine 24 has a floor 28 which is fixedly-spaced from its opposing tong face 8, and past which staples are ejected through staple guiding openings 30. Arms 20, 22 are formed of a relatively stiff and strong material, such as stainless steel several millimeters thick, and the spacing of each arm from the tongs is effected by adjustment of a thumbscrew 32 connected to a screw 34, of which upper screw 34 is visible, for setting a minimal stapler gap to accommodate tissue between the opposed anvil and staple head without damage.

The tongs 5 together with the stapler arms 20, 22 are all mounted as a unit, and attach by a spring-loaded push connection of the mounting 14 over a transverse pivot pin 15. When so attached, these structures are fitted within a pliars-like staple-driving mechanism. Specifically, a pair of staple driving arms 42, 44 aligned with receptacles 26 are actuated by squeezing handles 41, 43 to drive staples from the cartridges against the anvils 10. The cartridge (not shown) may be a conventional surgical staple cartridge, or a specially-dimensioned one of otherwise conventional design holding an array of staples of appropriate length and staple size. Preferably, as described further below in regard to FIGS. 3B–3E, the tongs and stapler arms are separable, to allow manipulation of a blood vessel thereabout in the course of the various steps of setting up the vessel for anastomosis utilizing the stapler device in accordance with the invention.

Figure 2:
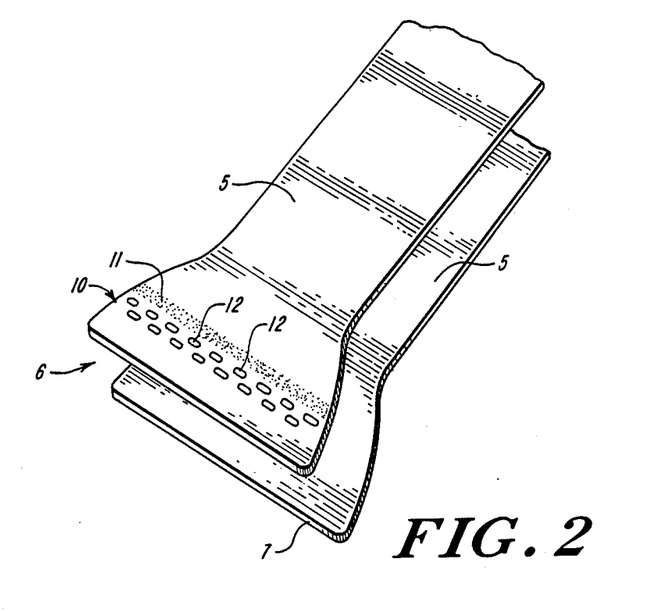
FIG. 2 is a detailed view of the vessel-gripping portion of the embodiment of FIG. 1.

The tongs 5 are illustrated in greater detail in FIG. 2. The gripping end 6 of each jaw is formed as a broad, essentially flat support surface with a smooth even end face 7. On the outer support surface a plurality of thin teeth or barbs 11 protrude from the surface and serve to grip and secure in position any tissue coming into contact with the surface. The gripping elements 11 are approximately 0.25–1.00 mm long, are extremely thin and stiff, and are of a length to grip but not perforate a vessel wall. Immediately adjacent to the gripping elements 11 is the rank 10 of staple-bending anvils, constituted by rounded depressions 12, which may be formed on a separate plate mounted on the tongs. The rank of staples is orthogonal to the long axis of the stapler arms, and preferably comprises two staggered rows to more effectively prevent leaks.

FIGS. 3A–3F illustrate an end-to-side anastomosis of a blood vessel performed with the stapler of FIGS. 1 and 2. A vessel B is cut to present a squared end, and a hole 50 is opened in the vascular wall of another vessel A. The length of the fenestration in vessel A is approximately one half of the circumference of the vessel B, or $\pi D/2$ where D is the diameter of vessel B. The vessel B which is to be anastomosed is then gripped by the tongs and its end 52 is everted over the opposed outwardly-directed anvil regions 10 to form a cuff 53 with the endothelial layer of the vessel facing outward. A pair of sutures 54, 56 are then started in the cuff at the edges of the anvil. During these steps, the tongs are separated from the rest of the stapler assembly to facilitate the manipulation of the blood vessel into position.

Next, the everted cuff 53 of vessel B, secured on the stapler anvil tongs 5, is inserted into the fenestration 50 of vessel A and the stapler arms 20, 22 are attached to the tongs and adjusted by thumbscrews 32 to bring the stapler magazines 24 down against the tissue of vessel A in the region to be stapled. Alignment pins (not shown) or other stapler registration means known in the art assure that each staple arm aligns correctly with its opposed tong and anvil face. The assembly is then mounted via mount 14 on the staple driver handle assembly 41, 42, 43, 44 (FIG. 1) and the handle is actuated to press two rows of staples from each staple head and thus connect the everted cuff 53 of vessel B to the side walls of vessel A along upper and lower linear regions. The two small openings that remain at the heel and toe of the opening 50 are closed by the U-shaped sutures 54, 56 that were placed earlier (FIG. 3C). The resulting end-to-side anastomosis, after withdrawing the stapler, is shown in FIG. 3F. In this anastomosis, the endothelium of vessel A is joined to the endothelium of vessel B, and no staples penetrate to the interior of either vessel or otherwise contact the bloodstream.

In another surgical procedure according to the present invention, an end-to-end anastomsis is effected in a topologically related way, and also results in an endothelium-to-endothelium autosuture with no direct staple-to-blood contact.

Figure 3A:
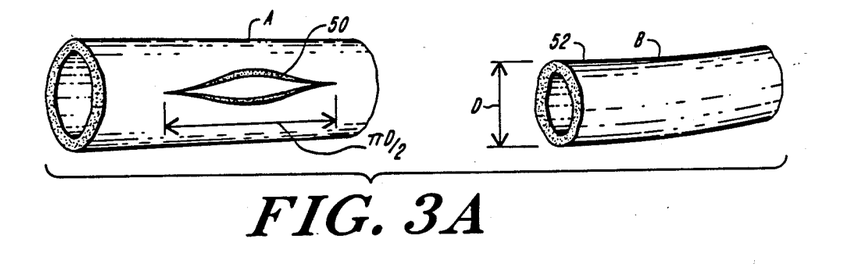
FIGS. 3A–3F illustrate steps of an end-to-side anastomosis performed in accordance with the invention.
Figure 3B:
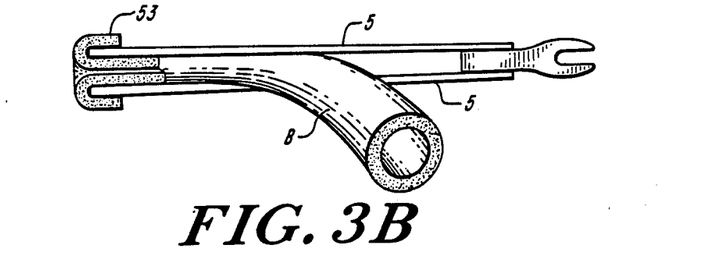
Figure 3C:
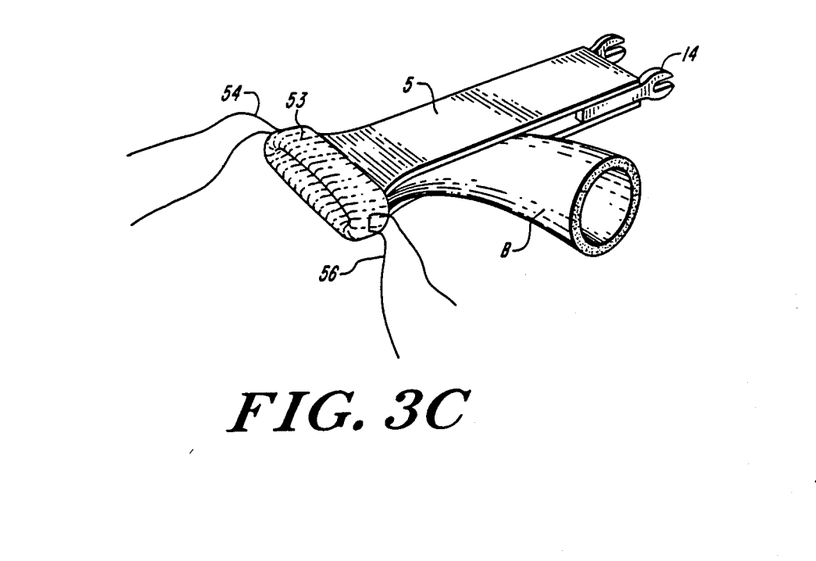
Figure 3D:
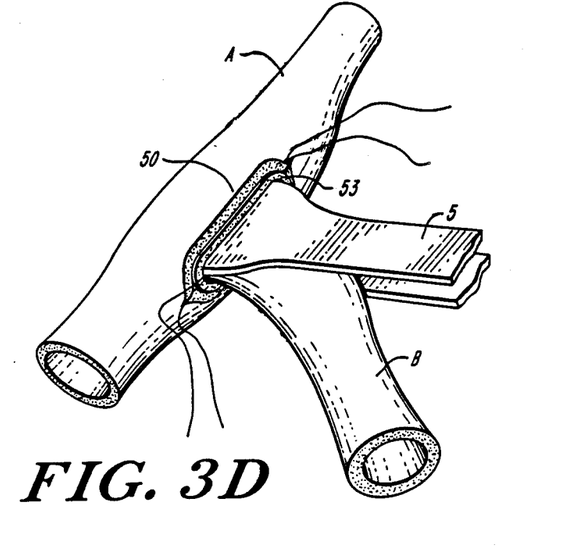
Figure 3E:
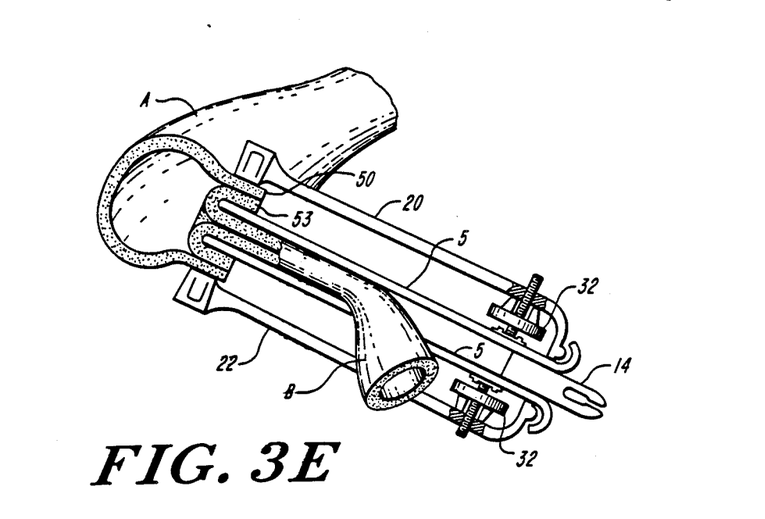
Figure 3F:
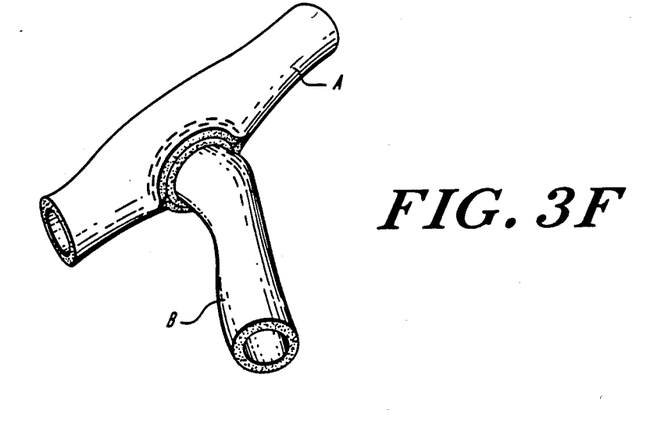
Figure 4A:
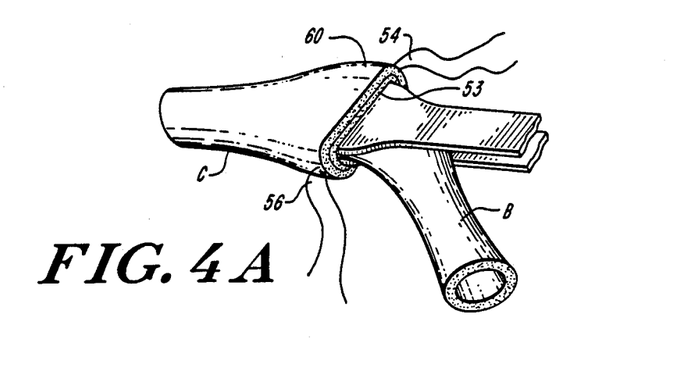
FIG. 4A–4C illustrate steps of an end-to-end anastomosis performed in accordance with the invention.
Figure 4B:
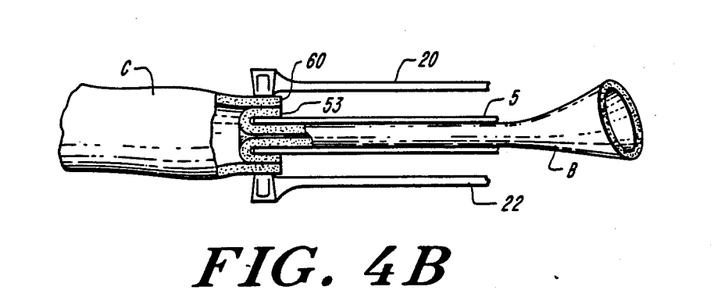
Figure 4C:
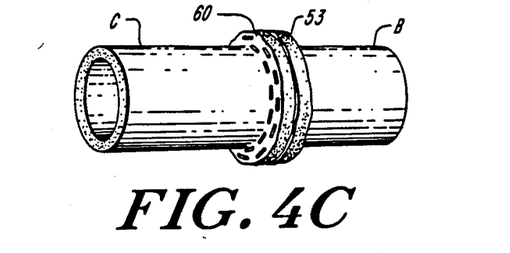

According to this aspect of the invention, after vessel B is prepared as shown in FIGS. 3B and 3C, the end 60 of a vessel C to which vessel B is to be joined is stretched over the anvil head and aligned with the everted cuff 53 as shown in FIG. 4A. The stapler arms are then attached and adjusted as shown schematically in FIG. 4B, with the everted portion of vessel B and the proximal end of vessel C positioned between the stapler heads and the opposed anvils. Pressing of the activation arms then drives two rows of staples from each head through the vessel walls, connecting the everted portion of vessel B to vessel C. As in the previous example, the two small openings left in the areas between the upper and lower linear ranks of staples are closed with two sutures on pledgets. The completed end-to-end anastomosis is illustrated in FIG. 4C.

Figures 5, 6A:
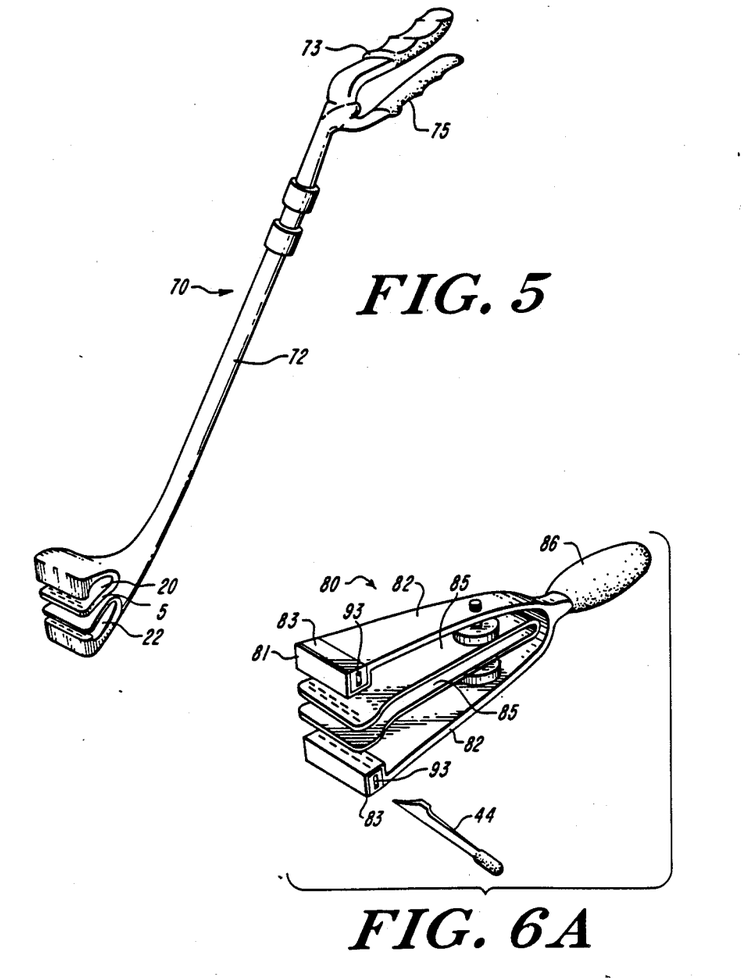
FIG. 5 illustrates second embodiment of stapler according to the invention.
FIGS. 6A–6E illustrate details of a third embodiment of a stapler according to the invention.

FIG. 5 shows a second embodiment 70 of a surgical stapling apparatus according to the invention. In this embodiment, the anvil tongs 5 and staple head 20, 22 are reduced in dimension to a size adequate to perform their tissue-gripping and cartridge-holding functions. In this embodiment, however, an elongate handle 72 is provided to hold and actuate these other elements. Handle 72 includes one or more mechanisms, such as lever-actuated rods or cables, or a fluid-driven actuator (not shown) for transmitting tissue-gripping or staple-driving pressure or control from operator actuated handpieces 73, 75 to the stapling mechanism. This embodiment advantageously requires very little clearance or working space at the anastomosis site.

FIGS. 6A–6E show construction details of a third embodiment 80 of the invention. In this embodiment, a pair of tongs 85 carry a pair of outwardly directed anvils similar to those of tongs 5 of the first-described embodiment. The tongs 85 have a fixed shank or handle 86 by which the instrument is manipulated, and are set up to receive upper and lower stapler arms 82, of which one is shown separately in FIG. 6B. A fork 87 at the end of each arm 82 engages a cross pin 88 to pivotally align the arm with a tong 85, and a thumbscrew 90 mounted on a bolt 91 in a T-slot 92 of the tongs threadedly engages the arm 82 to adjust its spacing from the anvil.

Figure 6B:
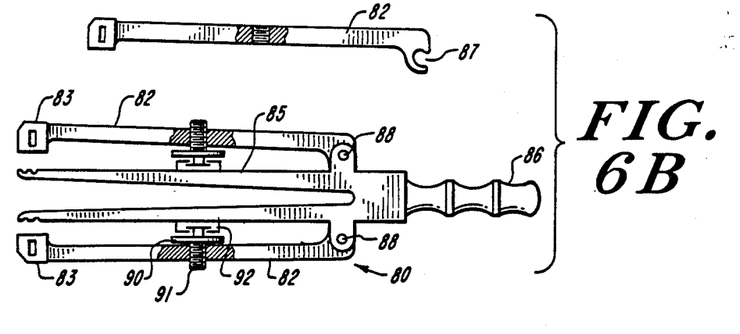

At the end of arm 82 opposite the fork 87, a magazine 81 or other holding means receives a pre-loaded cartridge 83 which contains an array of staples. As described in greater detail below, the staples are expelled from the cartridge without causing the arm to bear against the tissue by inserting a wedge-tipped drive bar 94 into a channel 93 in the cartridge 83, and advancing the drive bar through the channel transversely to the axis of the tongs.

Figures 6C, 6D:
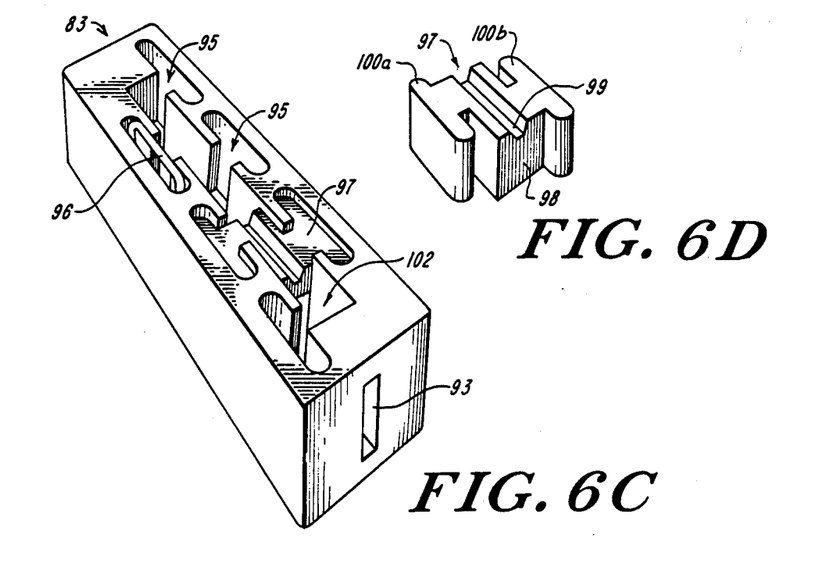
Figure 6E:
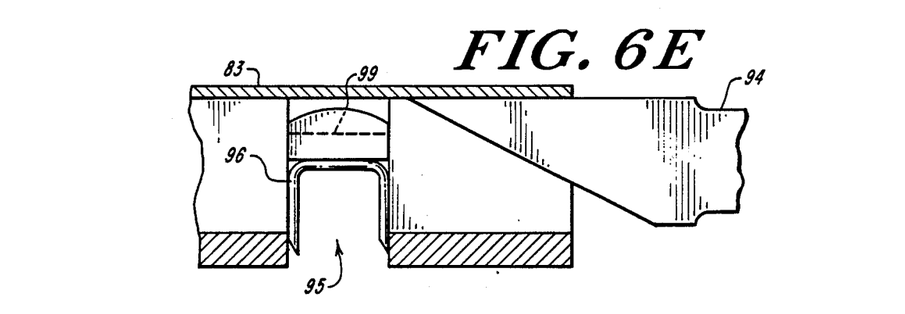

FIGS. 6C-6E show detailed views of the staple cartridge 83 and staple expelling mechanism. For clarity of illustration, a cartridge having two rows of three staples each is shown, although it will be understood that for an aortic stapler longer rows including perhaps seven to fifteen staples would be used.

Cartridge 83 is a molded substantially rectangular plastic block having two linear rows of vertically extending keyways 95 passing entirely through the block. Each keyway 95 holds and aligns a staple 96 oriented with its staple axis parallel to the long axis of the cartridge 83. The two rows of staples are offset, or staggered, from each other by approximately one half a staple width, so that they define an unbroken tissue closure line when applied to anastomose a vessel.

Over each offset pair of staples in adjacent rests a pusher block 97 (FIGS. 6C, 6D) which has a central body portion 98 with a groove 99 in its top or outer surface running along the axis of the rank of staples, and first and second runner blocks 100a, 100b extending from the central block 98 and precisely fitted to the two opposed keyways 95 of the two different ranks of staples. The runner blocks thus secure the sides of the cartridge 83 against lateral spreading. The groove 99 in the central block portion 88 is aligned with a central channel 102 extending along the middle of the cartridge, and also with the slot 93, so that when the wedge-tipped drive bar 94 is inserted into slot 93 it successively pushes down the pusher blocks 97, so that the runner blocks 100a, 100b eject successive pairs of staples 96 as the bar advances along channel 102. The pusher bar 94 may be formed of stainless or spring steel approximately 0.5-1.0 millimeters thick, and may be inserted by hand, or advantageously may be driven by mechanical means. While it is preferred to have cartridges 83 formed as separate disposable units which are inserted into stapler arms 82, it is also possible to form the arm 82 and cartridge 83 as a single disposable unit made of plastic.

In each of the foregoing embodiments, the end of a vessel is anastomosed by everting it over an outwardly facing anvil surface, placing a second vessel over the everted cuff and stapling against the anvil surface. While it may be desirable in some embodiments to interchange the positions of the stapler cartridge and the anvil, it is preferable in these embodiments to place the anvil on the central tongs, and the staple cartridge on the structure placed about the tongs. This configuration is selected, in part, to permit the tong structure to be as thin as possible, so that excessive stretching is not required to form the everted cuff.

In a different embodiment, the tongs are replaced by an elongated axial member, i.e., a cylinder, having an enlarged head or flange over which the vessel is everted. Such an embodiment is shown in FIGS. 7-10. In this embodiment, the first vessel is still passed through the member and everted over the end to form a cuff. However, unlike the embodiments of FIGS. 1-6, the anvil face is an angled or axially-directed circular face rather than a pair of radially directed linear segments. Further, as discussed below, the circular staple cartridge is preferably contained within the head over which the vessel is everted.

The novel topology for everting and gripping a vessel is achieved by providing a central passage extending through the stapler head, and forming the head structure in opposed sections so it may be removed from about the vessel after use. A vessel passes through the central passage, and its end is folded back over the enlarged head and secured, for example, by tying with a purse string. This provides an outwardly-facing endothelial layer entirely covering the circular anvil face. In other respects, this embodiment of the device has a structure quite similar to many end-to-end intestinal stapler devices, with a central shaft, ring-shaped stapler cartridge and staple-bending anvil, and circular cutter blade. However, as discussed further below, by everting the vessel over the head assembly, applicant's stapler provides a stapler which operates entirely from the outside of a tubular vessel or tissue structure. The resultant anastomoses are free of internal narrowing or internally-protruding staples.

Figures 7, 8:
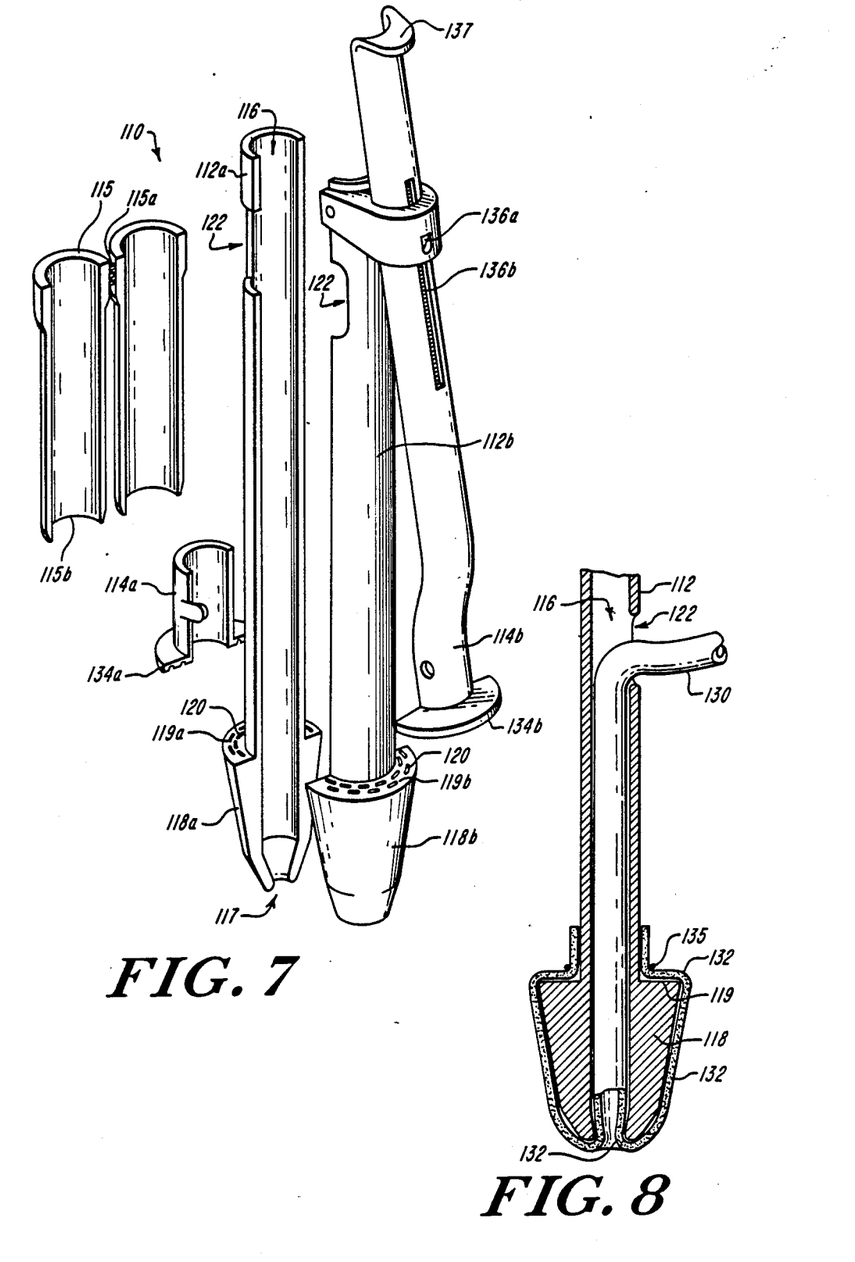
FIGS. 7–9 illustrate a fourth embodiment of a stapler according to the invention.

As shown in FIG. 7, an embodiment of 110 of this aspect of the invention includes a vessel securing structure 112a, 112b, a collar or base 114a, 114b and a circular knife 115 each of which is arranged in one or more separate parts which may be assembled together to form a basically cylindrical structure. The illustrated vessel securing structure has a pair of opposed half shells or arms which when placed together enclose a central passage 116 extending to the front end 117 of the structure. At end 117, each portion of the structure culminates in an enlarged head portion 118a, 118b which includes a back face 119a, 119b having a plurality of staple-guiding apertures 120 therein. A cut-out 122 in each portion of the structure combines to form an access opening to the interior passage 116. The back, or operator, end of the structure 112a, 112b may extend further to a common hinge (not shown) or to a collar or other adaptor which mounts it to a handle or otherwise openably secures the two halves together for use.

Skipping ahead briefly to FIG. 8, there is shown a sectional view through the gripping structure 112 formed of the opposed halves 112a, 112b with a blood vessel 130 placed therein for stapling. As shown, the end of vessel 130 is folded inside-out over the head 118 so that its endothelial tissue 132 faces outwardly over the head 118 and its stapling face 119. A purse string 135 secures the everted cuff of vessel tissue to the central shaft. Alternatively, a plurality of barbs or other gripping means might be used instead of the purse string. By way of scale, if the stapler is intended for use with a vessel of four to six millimeters diameter, the central passage 116 may be formed with a lesser diameter to accommodate the empty vessel, and the shoulder 119 may have an inner diameter of four to six millimeters and a width of one to three millimeters. For a given vessel, the relative sizes of these features are selected to accommodate the available elasticity of the vessel and to provide an adequate staple face 119 without occluding the vessel which, as will be seen with reference to FIG. 10A-10G, must pass through the ring of staples. The exemplary dimensions above may apply, for example, to a vessel for an aorta coronary bypass graft.

Returning now to FIG. 7, following the assembly of the vessel gripping structure 112 about a vessel, the collar or staple base structure 114, consisting of mating plates 134a, 134b is assembled together by snapping the two halves 114a, 114b together. A layer of tissue to which the vessel 130 is to be anastomosed is then brought into position over the staple face 119, and the base structure 114 is brought into position by the thumb grip 137 and secured by a linear gripping structure, illustrated by ratchet and tooth mechanism 136a, 136b.

Figure 9A:
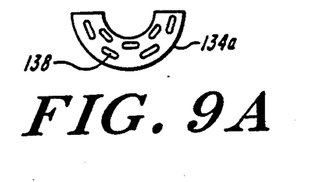

This places the plates 134a, 134b in alignment over the staple directing passages 120 for closing staples driven therethrough. FIG. 9A shows an axially directed view of a plate 134a, illustrating the curved depressions 138, of a conventional type for closing surgical fasteners It will be understood that where a two-part fastener is employed rather than a staple, plate 134a would instead be adopted to hold and apply one of the two mating parts of the fastener.

Continuing still with the description of FIG. 7, the last element shown is a circular knife 115, which in this embodiment includes opposed half portions hinged at hinge 115a. Knife 115 fits about the shaft of gripping structure 112, and is guided by the shaft so that when urged forward its cutting tip 115b cuts a circle against the face 119a, 119b of the head 118, radially inward of the staples, but of course outside of the vessel 130 which is entirely protected within the passage 116 of the gripping structure. The interior wall of the stapling base or collar 114a, 114b also guides the knife.

Figure 9B:
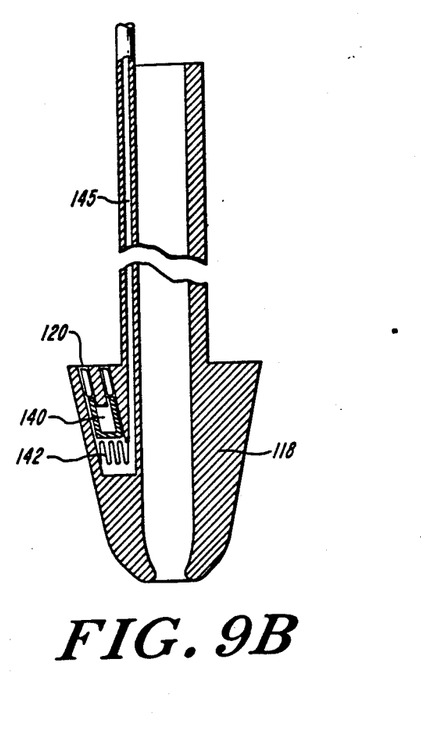

Preferably, as shown in FIG. 9B, the head 118 contains a pre-assembled staple cartridge 140 or chamber pre-loaded with staples and a staple pushing mechanism. The mechanism may include or be actuated by a diaphragm 142 which is moved by pressurized fluid provided via passage 145 from an operator controlled source via a trigger or other control mechanism. The pre-loaded staple chamber or cartridge 140 is semicircular, and the staple directing passages 120 are aligned with the corresponding portions of the base plates 134a, 134b.

Turning now to FIGS. 10A–10I, the steps of performing end-to-end and end-to-side anastomoses with this apparatus are shown in some detail.

Figure 9C:
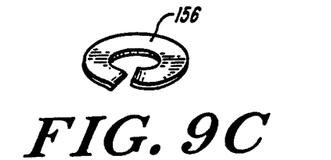
Figure 10A:
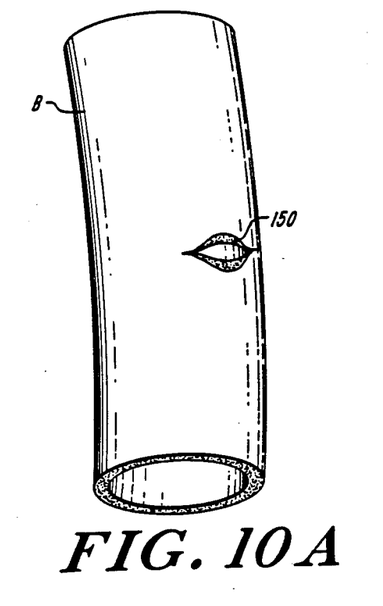
FIGS. 10A–10G and 10H–10I illustrated end-to-side and end-to-end anastomoses performed with the stapler of FIGS. 7–9.
Figure 10B:
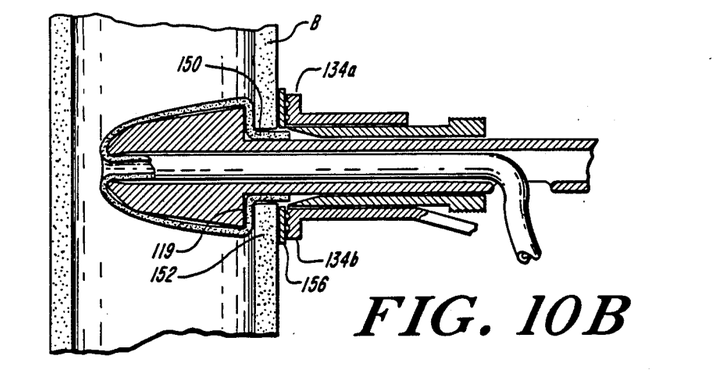

FIGS. 10A–10G illustrate the end-to-side anastomosis of a small vessel 130 to a larger vessel, denoted B, which may, for example, be the aorta. The intermediate steps are shown in section to better illustrate stapler operation. As shown in FIG. 10A, first an incision 150 having a length approximately the diameter of the smaller vessel is made in vessel B. The tip of the vessel gripping structure with vessel 130 attached thereto, as shown in FIG. 9, is then inserted through the slit, and the base plate 134a, 134b is brought down into position over the wall 152 of vessel B about the opening 150 so that the everted cuff of vessel 130 and the interior wall of vessel B are in contact between the staple face 119 and the base plate 134. Preferably, a radioopaque pledget 156 which is formed, for example, of Teflon felt is first placed about the shaft. The pledget is formed as a split washer, as shown in FIG. 9C.

Figure 10C:
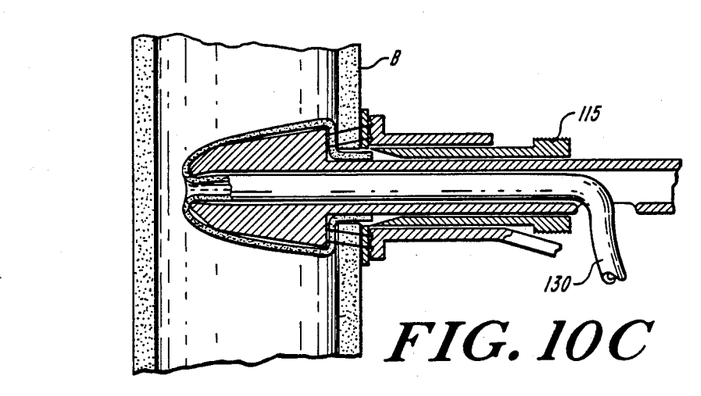
Figure 10D:
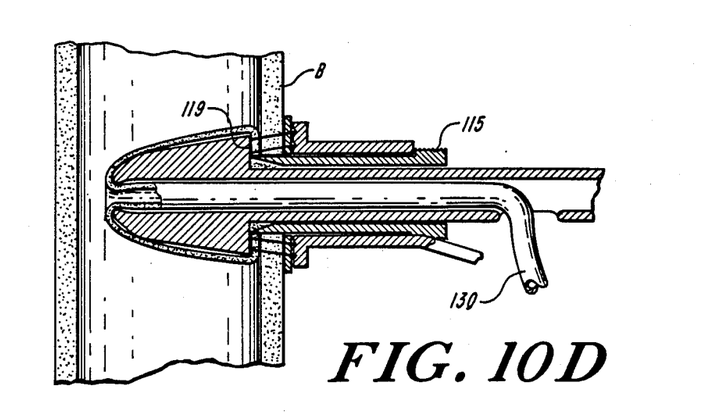
Figure 10E:
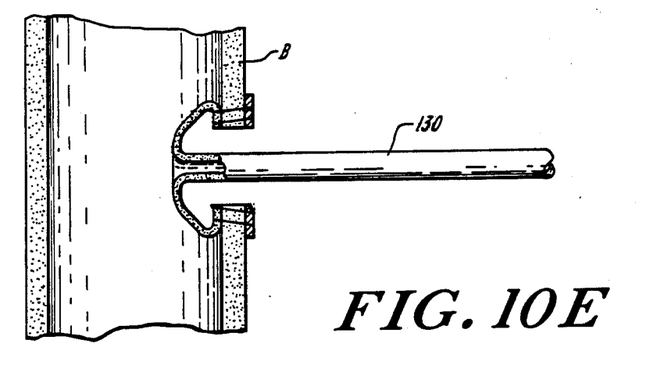
Figure 10F:
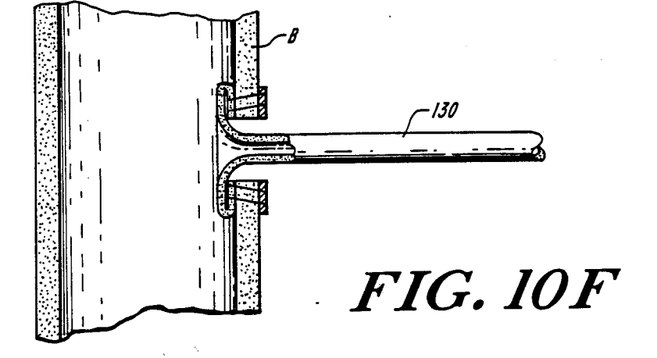
Figure 10G:
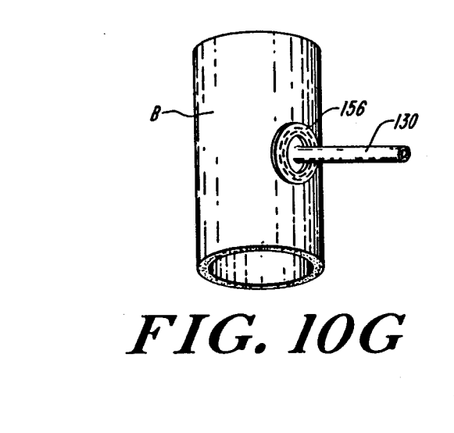

The stapler is then actuated to place a double rank of staples in a circular ring as shown in FIG. 10C. After stapling, knife 115 is brought down against face 119, as illustrated in FIG. 10D, to trim a perfectly circular opening in vessel B and cut off the end remnants of vessel 130. The stapler elements 114, 115 are then disassembled and the structure 112 is withdrawn from the site, leaving the vessel 130 fully sutured to and loosely extending into vessel B (FIG. 10E) vessel 130 is then pulled taut (FIG. 10F). The resulting anastomosis, unlike convention circular staple anastomoses as employed in intestinal surgery, has no exposed staple surfaces in the interior of the vessel and does not reduce the vessel diameter at the anastomosis site. FIG. 10G shows a perspective view of the complete anastomosis.

It will be appreciated that the structure and method shown in FIGS. 7-10 is not limited to end-to-side anastomoses, or to anastomoses of vessels of differing diameters.

Figure 10H:
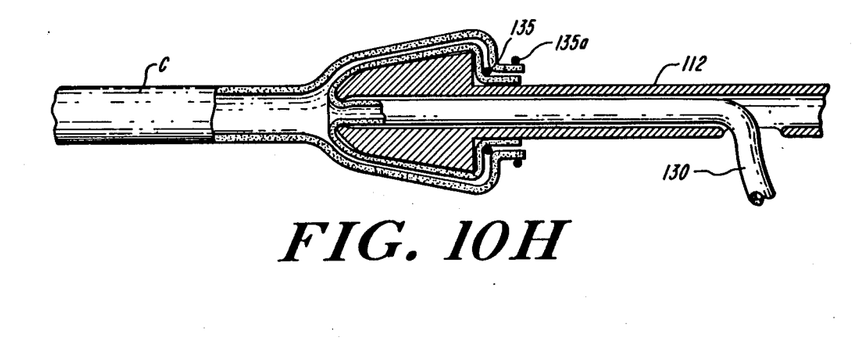
Figure 10I:
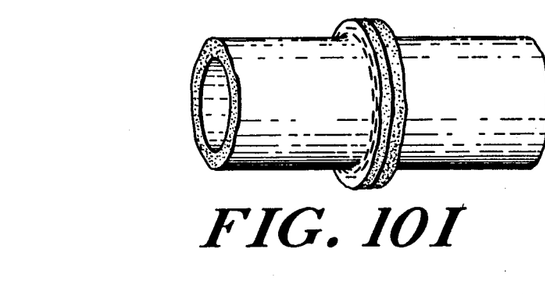

FIG. 10H shows, by way of example, the manner in which vessel 130 would be end-to-end stapled to a vessel C of comparable diameter In this case, the end of vessel C is fitted over the head 118 and secured to the shaft with a second purse string 135a before stapling After clamping, stapling, cutting, withdrawal of the instrument and pulling axially as described above, the resulting staple junction, shown in FIG. 10I, has a complete ring of staples about the exterior of the vessel with no staple surface exposed to the interior, no narrowing of the vessel, and no need for manual suturing.

Thus, the invention provides a novel apparatus and method for stapling tubular tissue, generally referred to herein as vessels, and provides a particularly advantageous class of instruments and techniques for joining blood vessels.

The invention being thus disclosed, and several instruments and methods of practice of the invention being thus described, modifications and variations will occur to those skilled in the art, and such modifications and variations are intended to be within the scope of the invention, as defined by the claims appended hereto.

What is claimed is:

1. A surgical stapler comprising
   an elongated instrument body extending along an axis and having an interior axial passage for passage of a tubular member therethrough and an enlarged head such that an end of the tubular member may be everted over the head and secured about the instrument body,
   a collar structure removably placeable about the instrument body adjacent the head,
   a circular staple cartridge and a circular staple anvil each contained in a different one of said head and said collar structure, and
   means for driving staples against the anvil to staple the everted end of the tubular member to a layer of tissue placed between said head and said collar structure
   said instrument body being formed in plural separable parts for allowing placement of said tubular member in and removal of said tubular member from said interior axial passage.

2. A stapler according to claim 1, further comprising a circular knife located radially inward from said circular staple cartridge for trimming material located topologically outside of said tubular member.

3. A stapler according to claim 2, wherein said means for driving includes a non-rigid coupling means.

4. A stapler according to claim 1, wherein said set of tongs comprises a pair of half-cylindrical tip members.

5. In a stapler of the type where in a first tubular tissue structure is secured over the head of a shaft having an axis oriented parallel to the first tissue structure for anastomosis to a second tissue structure, the improvement where in the shaft is formed of opposed portions enclosing a central interior passage extending along the axis, and the first tubular tissue structure passes through the central interior passage to be everted over the head so that the inner surface of the first tissue structure faces outwardly along a region of the head where it is placed against the second tissue structure, and a split ring about said shaft is opposed to said region, said split ring and said head each accommodating one of an anvil or a staple means which cooperate to join said first and second tissue structures with a row of staples at said region.

6. The improvement of claim 5, wherein the stapling region is a circular stapling region.

7. A surgical stapler comprising
a handle extending along an axis,
a vessel gripping structure having opposed first and second outwardly facing portions at an end thereof, said end being shaped and dimensioned such that a blood vessel may pass along the axis through the interior of the structure and be everted to form a cuff over the outwardly-facing portions,
a staple base structure aligned with the outwardly facing portions of said vessel gripping structure, said staple base structure being fitted about a portion of the structure through which the blood vessel passes so that said outwardly-facing portions and said base structure each surround the blood vessel while securing the cuff therebetween,
means for adjusting the spacing between said staple base structure and said outwardly-facing portions to accommodate a desired thickness of vessel tissue without applying destructive pressure to the cuff, and
means for driving staples between the base structure and the outwardly-facing portions through said cuff to autosuture tissue to said cuff.

8. A stapler according to claim 7, wherein the end of the vessel gripping structure includes a head portion with a staple cartridge holding at least one row of staples oriented substantially along the direction of a blood vessel held in said vessel ripping structure.

9. A stapler according to claim 8, further comprising a circular knife.

10. A stapler according to claim 7, wherein the jaws are dimensioned to accommodate a blood vessel having a diameter under approximately one centimeter.

11. A surgical stapler comprising
a set of tongs having a central axial passage for passage of a tubular member therethrough and an enlarged head comprised of a pair of half-cylindrical tip members such that an end of the tubular member may be everted over the head and secured,
a collar structure removably placeable about the tongs adjacent the head,
a circular staple cartridge and a circular staple anvil each contained in a different one of said head and said collar, and
means for driving staples against the anvil to staple the everted end of the tubular member to a layer of tissue placed between said head and said collar structure.

12. A surgical stapler comprising
a set of tongs having a central axial passage for passage of a tubular member therethrough and an enlarged head such that an end of the tubular member may be everted over the head and secured,
a collar structure removably placeable about the tongs adjacent the head,
a circular staple cartridge and a circular staple anvil each contained in a different one of said head and said collar.
means for driving staples against the anvil to staple the everted end of the tubular member to a layer of tissue placed between said head and said collar structure, said means for driving including non-rigid coupling means, and
a circular knife located radially inward from said circular staple cartridge for trimming material located topologically outside of said tubular member.

13. A surgical stapler comprising
a set of tongs extending along an axis and defining an axial passage centrally between said tongs for a blood vessel extending therealong, said tongs having at one end a pair of vessel gripping jaws sized for everting the end of the blood vessel to form a cuff supported by said jaws, each said jaw including an outwardly facing anvil portion adjacent said one end,
a structure mounted about the tongs to position surgical staples in alignment over the anvil portions.
means for setting a spacing between the tongs and the structure to accommodate a tissue layer placed over said cuff, and
means for driving the surgical staples against the anvil portions to join the tissue layer and cuff thereby anastomosing the blood vessel segment to the tissue layer.

14. A surgical stapler according to claim 13, wherein each said gripping jaw includes means for gripping the vessel to secure the cuff in position.

15. A surgical stapler according to claim 13, wherein said arm structure supports a plurality of staples in a row facing the axis of the blood vessel segment.

16. A surgical stapler according to claim 15, wherein the jaws are sized to grip and support an aorta.

17. A surgical stapler according to claim 15, wherein said tongs, said arm structure and said means for driving are each separate parts which may be assembled together in operative relation after forming said cuff on the tongs.

18. A surgical stapler comprising
a vessel gripping structure having opposed first and second outwardly-directed anvils at gripping jaws thereof, said jaws defining a channel extending along an axis therebetween for passage of a vessel through said channel, said jaws being dimensioned such that an end of the vessel exiting said channel may be everted to form a cuff over the anvils,
a pair of surrounding members aligned with said vessel gripping structure, each surrounding member having a staple-holding head portion which holds a plurality of surgical staples aligned with a corresponding one of said first or second anvils so that the staples are closed when driven against a said anvil,
means for adjusting the spacing between said pair of surrounding members and said anvils to accommodate a desired thickness of vessel tissue without destrictive pressure, and
means for driving the staples of each staple holding head against the anvil aligned therewith to autosuture tissue to said cuff.

19. A stapler according to claim 18, wherein each said staple-holding head portion includes a cartridge holding at least one row of staples and an alignment frame into which said cartridge fits, and is oriented along an axis substantially orthogonal to a blood vessel held in said vessel gripping structure.

20. A stapler according to claim 19, wherein the cartridge has a central passage extending the length thereof above the staples, such that motion of a drive member along the passage is effective to drive the staples against a said anvil.

21. A stapler according to claim 18, wherein the jaws are dimensioned to accommodate an aorta.

* * * * *

UNITED STATES PATENT AND TRADEMARK OFFICE
CERTIFICATE OF CORRECTION

PATENT NO. : 4,930,674
DATED : June 5, 1990
INVENTOR(S) : Jacob H. Barak

It is certified that error appears in the above-identified patent and that said Letters Patent is hereby corrected as shown below:

Column 1, line 44, please delete "il is an object o(" and insert --it is an object of--.

Column 7, line 5, before "It" please insert --.--.

Column 8, line 5, before "In" please insert --.--.

Column 8, line 7, after "stapling" please insert --.--.

Signed and Sealed this

Tenth Day of December, 1991

Attest:

HARRY F. MANBECK, JR.

*Attesting Officer*     *Commissioner of Patents and Trademarks*